United States Patent [19]
Guibert

[11] 4,339,928
[45] Jul. 20, 1982

[54] FREEZING UNIT FOR PRE-COOKED FOOD PACKAGES

[76] Inventor: Raul Guibert, 10374 Summer Holly Cir., Los Angeles, Calif. 90024

[21] Appl. No.: 207,197

[22] Filed: Nov. 14, 1980

Related U.S. Application Data

[60] Continuation-in-part of Ser. No. 97,787, Nov. 27, 1979, Pat. No. 4,307,286, which is a continuation-in-part of Ser. No. 971,381, Dec. 20, 1978, which is a division of Ser. No. 809,775, Jun. 24, 1977, Pat. No. 4,132,216, which is a continuation-in-part of Ser. No. 776,772, Mar. 11, 1977, Pat. No. 4,112,916, which is a continuation-in-part of Ser. No. 825,037, Aug. 16, 1977, Pat. No. 4,269,169.

[51] Int. Cl.³ .................................... F25D 25/00
[52] U.S. Cl. ................................. 62/62; 62/456; 62/457; 62/237; 62/382; 34/196
[58] Field of Search ............... 62/62, 237, 382, 457, 62/452, 456, 239, 266, 419; 34/196; 126/261

[56] References Cited

U.S. PATENT DOCUMENTS

| 2,314,301 | 3/1943 | Williams | 62/62 X |
|---|---|---|---|
| 2,507,834 | 5/1950 | Storer et al. | 62/456 X |
| 3,261,650 | 7/1966 | Stromquist | 34/196 R |
| 3,545,223 | 12/1970 | Elland | 62/237 |
| 3,866,435 | 2/1975 | Frank et al. | 62/382 |
| 4,052,589 | 10/1977 | Wyatt | 62/457 X |
| 4,126,775 | 11/1978 | Wyatt | 34/196 |

FOREIGN PATENT DOCUMENTS 54-5258 1/1979 Japan ........................ 62/62

Primary Examiner—Lloyd L. King
Attorney, Agent, or Firm—Michael Ebert

[57] ABSTRACT

A freezing unit for use in a cold chamber to effect freezing of a load of pre-cooked food packages at a rate more rapid than the freezing rate of that load that would take place in the chamber in the absence of the unit. The unit includes a vertical plenum provided with a perforated wall and having an open input and a closeable output. The food packages are stacked in a rack adjacent the perforated wall of the plenum, with air spaces between the packages. Cold air drawn from the chamber atmosphere at a temperature below the freezing point of the food is forced into the input of the plenum to produce a positive pressure therein when the output is closed, thereby causing the pressurized cold air to penetrate the perforated plenum wall and pass through the air spaces in the stack at high velocity, the air returning to the cold chamber whereby rapid cooling of the packages is effected. By periodically opening and closing the plenum output, the cold air flowing through the air spaces assumes the form of air pulses separated by no-flow intervals to produce a heat transfer pattern within the food body in each package that results in a reduction in temperature which becomes substantially uniform throughout the body at a level close to the freezing point, whereby the body is caused to freeze, not in successive layers, but almost in toto within a short period, thereby avoiding the formation of large ice crystals.

20 Claims, 13 Drawing Figures

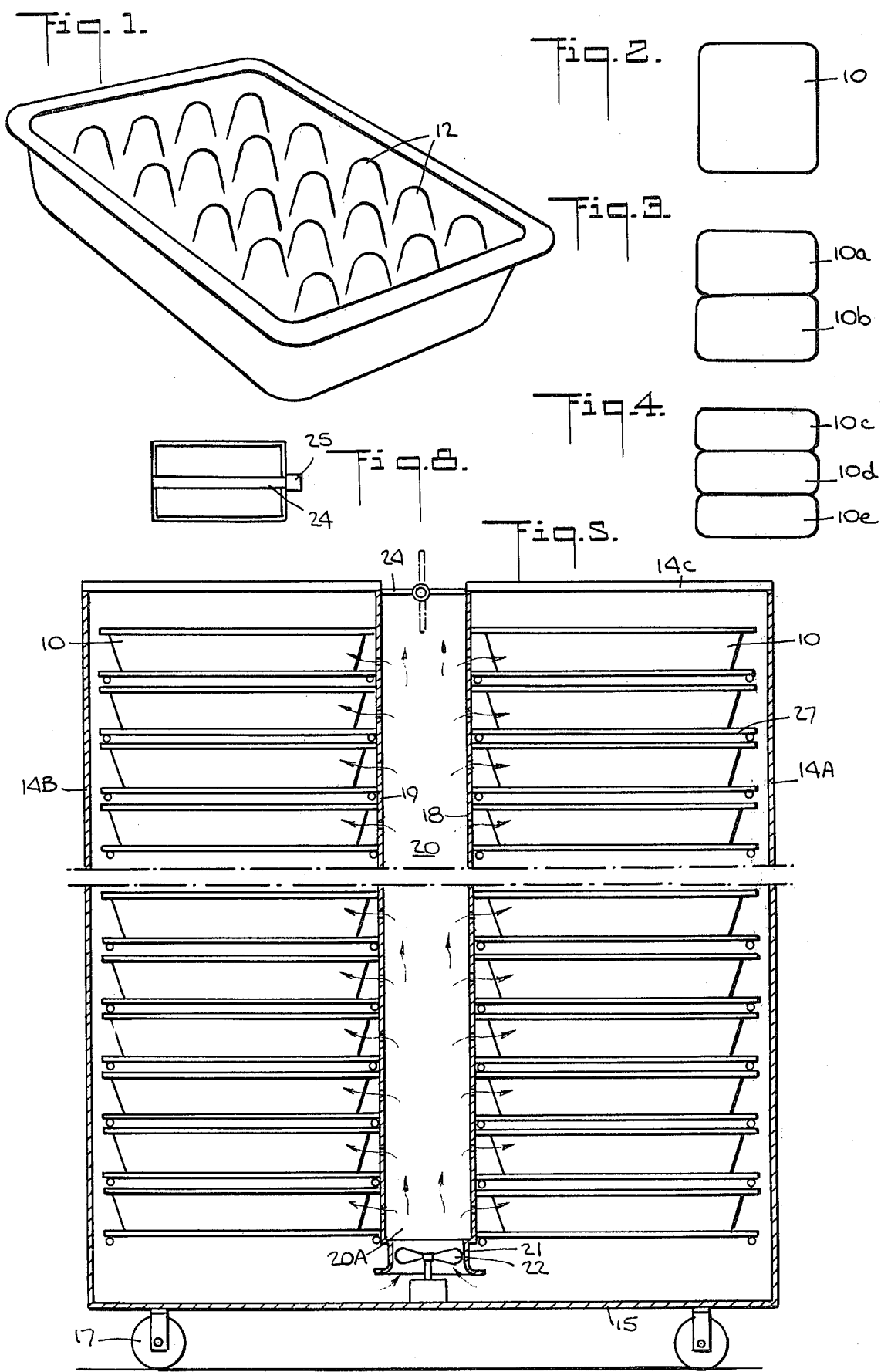

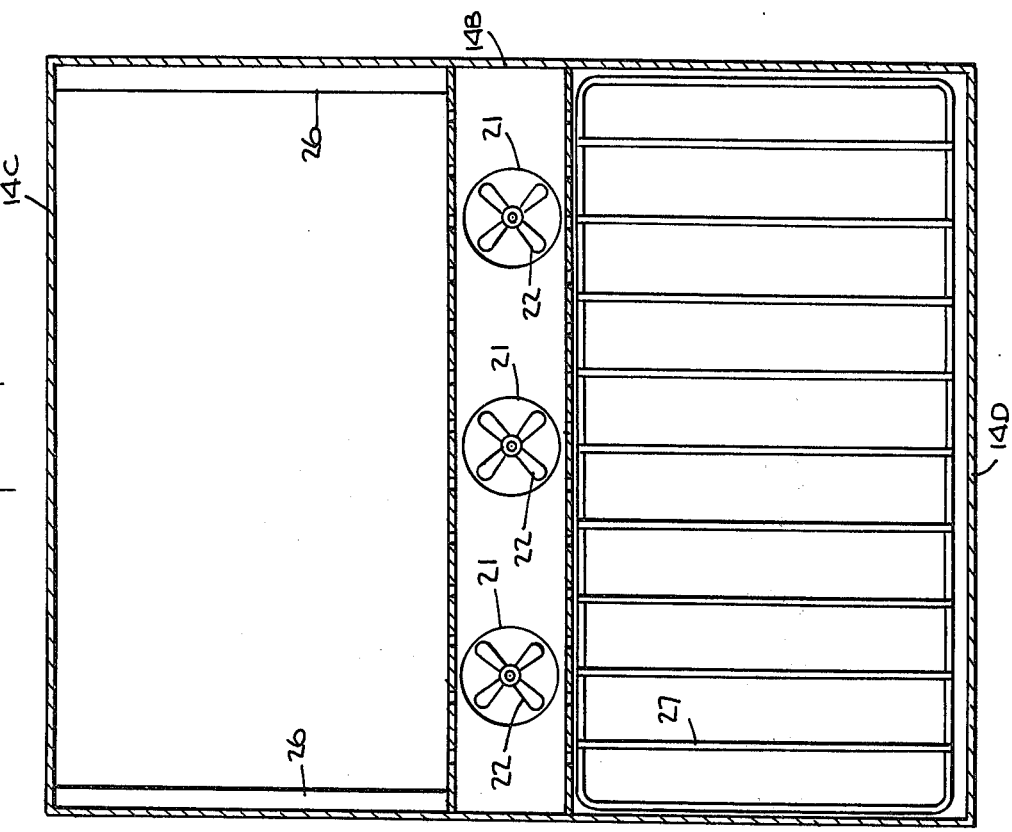
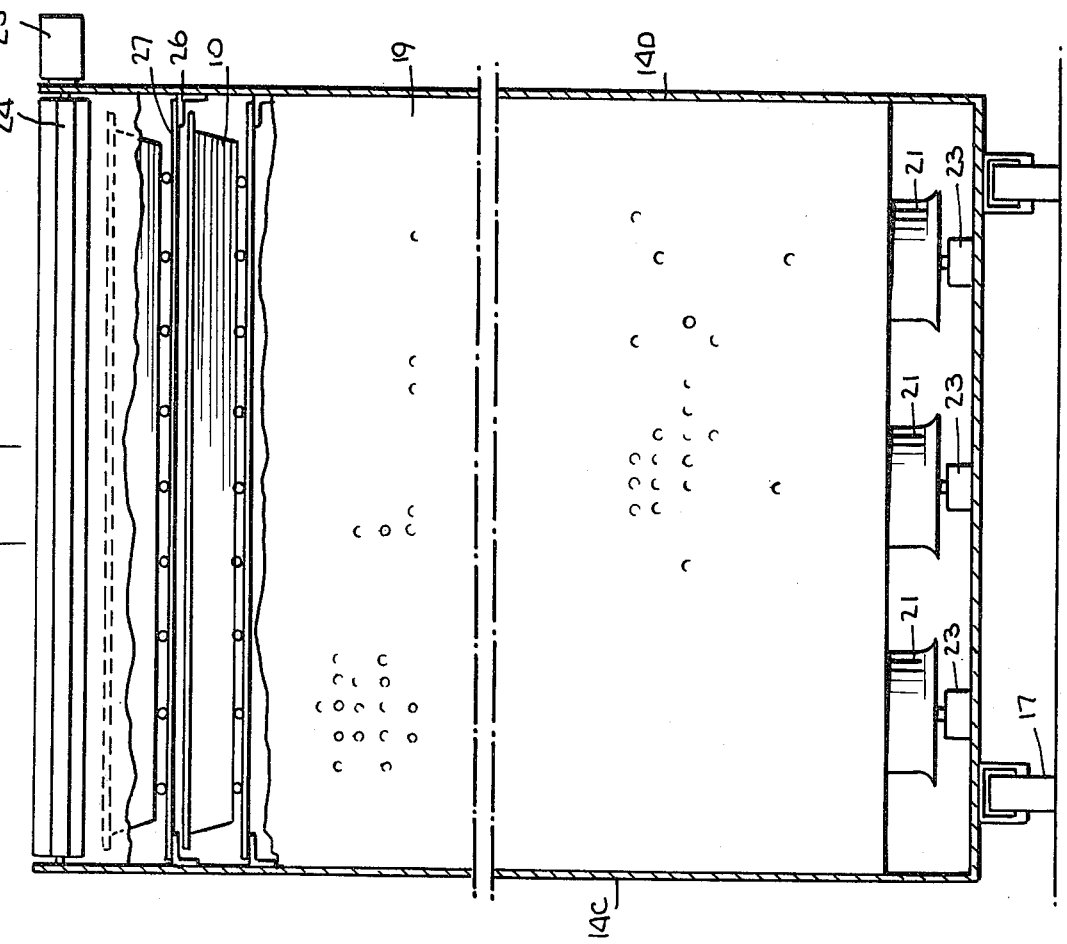

FREEZING UNIT FOR PRE-COOKED FOOD PACKAGES

RELATED CASES

This application is a continuation-in-part of my copending application Ser. No. 097,787, filed Nov. 27, 1979, now U.S. Pat. No. 4,307,286, which is a continuation-in-part of my copending application Ser. No. 971,381, filed Dec. 20, 1978, which is a division of an earlier application Ser. No. 809,775, filed June 24, 1977, entitled "Two-Zone Hot Air Oven for Food Loaded Cartridges," now U.S. Pat. No. 4,132,216, dated Jan. 2, 1979, which in turn is a continuation-in-part of an original application Ser. No. 776,772, filed Mar. 11, 1977 entitled "Hot Air Oven for Food-Loaded Cartridges", now U.S. Pat. No. 4,112,916, dated Sept. 12, 1978 which in turn is a continuation-in-part of application Ser. No. 825,037, filed Aug. 16, 1977, issued on Aug. 26, 1981 as U.S. Pat. No. 4,269,169. The entire disclosures of these related cases are incorporated herein by reference.

BACKGROUND OF INVENTION

This invention relates generally to apparatus for cooling packages containing pre-cooked food products, and more particularly to a freezer unit for use in a cold chamber and adapted to contain a load of such packages with air spaces therebetween, the unit functioning to draw cold air from the atmosphere of the chamber and to circulate this air within the unit to cause it to flow at high velocity in the air spaces to promote rapid cooling of the food products.

The above-identified related patent applications disclose a convenience food technique and apparatus therefor in which pre-cooked meals which have been kept under refrigeration are thereafter reheated in a hot air oven and made directly available to customers. The nature of the cooking, refrigeration and reheating operations are such that the essential texture, flavor and nutritional value of the food are maintained without significant degradation.

In this convenience food technique, each cooked meal is placed in an individual tray and sealed, a stack of such trays being nested within an open carton to form a cartridge which facilitates subsequent handling and processing. The side walls of the carton are provided with holes to admit heated or low temperature air which is circulated in the spaces between the trays in the stack to heat or cool the meals therein, as the case may be.

These cartridges, prior to being placed in an oven for reheating the pre-cooked meals, must be kept in a refrigerated storage chamber to maintain the food temperature just above the freezing point for as long as is necessary. In practice, this temperature may be in the range of about 12° to 30° F.; for when the moisture content of the food is rich in dissolved salts, the freezing point may be well below 32° F. It is important that the trays be sealed to prevent the loss of moisture and volatile constituents.

In the large scale production of cooked meals in connection with a convenience food technique of the type disclosed in the related patent applications, after the meals have been cooked and placed in sealed trays, it is essential that the temperature of the hot meals in the trays be reduced in temperature quickly to a level approaching the cold temperature of the refrigerated chamber in which the trays are to be stored. To this end, a blast tunnel may be used, but this is costly to operate, particularly for small production runs.

In a prior attempt to accelerate the action of a conventional freezing system and to overcome certain shortcomings thereof, the Overbye U.S. Pat. No. 3,115,756 discloses an arrangement in which the food to be cooled or frozen is conveyed through an open tunnel on a foraminous belt below which are disposed the evaporation coils of a mechanical refrigeration system. Air is blown upwardly through the coils and the resultant cold air is then forced through the belt to effect rapid cooling of the food advancing through the tunnel.

While the Overbye arrangement is more efficient than most blast tunnel freezers, it has serious drawbacks, among which is the formation of snow and ice on the refrigeration coils and other components of the system as a result of moisture extracted from the food being processed and from the ambient air. The formation of such snow and ice markedly reduces the thermal efficiency of the refrigeration system.

Thus in a convenience food operation, various meals to be later served on demand are first cooked and then deep-frozen and stored. When an order is placed for a particular meal, the selected item is withdrawn from the freezer and then thawed and reheated. A particular concern of the present invention are convenience food operations carried out in institutional, cafeteria and other mass-feeding facilities wherein various entrees are pre-packed and pre-cooked in steamable trays. Typical convenience food products for this purpose are frozen pasta entrees prepared by Buitoni Food Service of Hackensack, N.J. One such entree takes the form of beef-stuffed pasta shells, twenty such frozen shells being contained in a single steamable tray.

The term "steamable tray" refers to a flanged tray of rectangular form made of aluminum foil and having a removable foil cover to seal the tray. Such trays come in standard sizes but in different depths for use in conjunction with steam tables or bains-marie, these being tables having openings therein to receive and hold trays of cooked food over steam or hot water circulating beneath them.

The term "pre-cooked food package" as used herein encompasses the sealed trays of the type disclosed in the above-identified related patent applications in which the tray also functions as the serving plate, the sealed "steamable" trays in commercial use in which the food must be transferred to plates, and any other form of sealed tray or pan containing a pre-cooked meal or food product.

It is essential when freezing a meal that has just been cooked that freezing take place within a relatively brief period; for the longer it takes to effect the necessary freezing, the greater is the danger of deleterious bacterial activity that might spoil the product. Thus, assuming the availability of a convenional walk-in freezer closet or cold chamber in a cafeteria or institutional mass-feeding institution, should a load of pre-cooked food packages being placed in the chamber whose atmosphere is cold air, in the typical chamber it will ordinarily take 12 to 14 hours before the load is frozen.

A prolonged cool-down period is not only unacceptable in terms of bacterial activity, but the long term presence of a load of pre-cooked food packages in the chamber pre-empts a considerable space in the chamber which is then not available for storing other food products requiring refrigeration, such as meats and vegetables.

Moreover, a protracted cool-down period can also be destructive of the texture of the pre-cooked food products. With freezing, the water or moisture content of the food is converted into ice crystals, the size of the crystals being a function of freezing time. When freezing occurs gradually, large ice crystals are formed which act to rupture the internal structure of the food product, and in some cases to render it mushy and unpalatable. Fast-freezing, on the other hand, gives rise to much smaller ice crystals with minimal destructive effects.

With existing freezing techniques, it is not possible in the context of a typical walk-in cold chamber or similar refrigeration facility to effect rapid and non-destructive freezing of pre-cooked food packages. The reason for this drawback is attributable to two heat transfer factors, flow velocity and film coefficient.

The process by which a package of pre-cooked food at a temperature above ambient is lowered in temperature to a freezing level involves the transfer of heat from a point at a high temperature to a point of low temperature. Methods of heat transfer include conductive heat flow through solids and liquids, and convection currents in fluids.

In thermal convection, heat is transferred by the movement of fluid matter; whereas in conduction, atoms or molecules simply pass on the kinetic energy delivered to them. In either case, the rate of heat transfer depends on the temperature gradient and the cross-sectional area of the heat transfer path.

When heat is carried away by forced convection from a warm food package by a stream of cold air, the greater the air velocity, the more rapid the cooling process. The static cold air in the typical cold chamber does not provide a high velocity stream which promotes freezing. Moreover, a conduction factor also comes into play in the cooling process, for a thin layer of fluid remains stagnant against the interface of the cold air stream and the warm body being cooled. This film, in effect, becomes another conducting layer outside of which the fluid stream temperature exists.

Though this stagnant film is extremely thin, its resistance to heat transfer is usually high compared to heat flow in a solid body. Thus a heat exchanger in which the solid material is a highly conductive metal, the film at the interface introduces significant heat flow resistance between the metal body and the fluid in heat exchange relation therewith. When, however, the body of food being frozen is in a sealed package which is placed in a cold air stream that flows past the surface of the package at high velocity, this tends to dislodge any film at the external surface of the package. However, as will hereinafter be explained in greater detail, internal films are formed in the packaged body of food which militate against rapid heat transfer. These internal films slow down the freezing process and result in the formation of large ice crystals.

SUMMARY OF INVENTION

In view of the foregoing, the main object of this invention is to provide a freezer unit usable in a conventional cold chamber and adapted to contain a load of pre-cooked food packages, the unit functioning to draw cold air from the atmosphere of the chamber and to circulate this air within the unit to cause it to flow at high velocity in the air spaces between the packages to promote rapid cooling of the food products.

More particularly, an object of this invention is to provide a freezer unit of the above type in which the cold air circulating through the unit is in pulsatory form to subject the surface of the packages to high velocity air surges separated by no-flow intervals in a manner creating a heat transfer pattern that results in a reduction in food temperature which becomes substantially uniform throughout the body when the level of temperature is close to the freezing point, whereby the body then freezes almost in toto within a short period.

A significant feature of the invention resides in the fact that a given load of pre-cooked food packages, when housed in the freezing unit and placed in a conventional cold chamber, will be frozen at a much more rapid rate than the same load placed in the chamber without the unit, thereby minimizing the formation of destructive ice crystals. Bacterial activity resulting from a protracted freezing time is avoided; and, because freezing is so rapid, the food load is in the cold chamber for a relatively brief period, and the space occupied by the unit is quickly made re-available for other products to be refrigerated.

Also an object of this invention is to provide a freezer unit specially adapted to accommodate steamable trays.

A further object of this invention is to provide a freezer unit especially adapted to accommodate cartridges in which a group of hexagonal trays is stacked within a carton.

Yet another object of the invention is to provide an efficient and reliable freezing unit which may be manufactured at low cost.

Briefly stated, these objects are accomplished in a freezing unit for use in a cold chamber to effect freezing of a load of pre-cooked food packages at a rate more rapid than the freezing rate in the absence of the unit. The unit includes a vertical plenum provided with a perforated wall and having an open input and a closeable output, and means to draw cold air from the chamber and force it into the input of the plenum.

The food packages are stacked in a rack adjacent the perforated wall of the plenum, with air spaces between the packages. When cold air is forced into the input of the plenum, it produces a positive pressure therein when the output is closed, thereby causing the cold air to penetrate the perforated plenum wall and to flow through the air spaces in the stack at high velocity, the air returning to the cold chamber whereby rapid cooling of the packages is effected.

By periodically opening and closing the plenum output, the cold air flowing through the air spaces assumes the form of air pulses separated by no-flow intervals to produce a heat transfer pattern within the food body in each package that results in a reduction in body temperature which becomes substantially uniform throughout the body at a level close to the freezing point, whereby the body is caused to freeze, not in successive layers from the outside to the core, but almost in toto within a short period, thereby avoiding the formation of large ice crystals.

OUTLINE OF DRAWINGS

For a better understanding of the invention as well as other objects and further features thereof, reference is made to the following detailed description accompanied by the following drawings in which:

FIG. 1 is a perspective view of a typical full-size steamable tray containing frozen meals;

FIG. 2 shows in reduced scale rectangular dimensions of the full-size steamable tray;

FIG. 3 shows the rectangular dimensions of the two half-size trays;

FIG. 4 shows the rectangular dimensions of three one-third size trays;

FIG. 5 is a somewhat schematic longitudinal section taken through the freezer unit in accordance with the invention for steamable trays;

FIG. 6 is a longitudinal section taken through the center of FIG. 5;

FIG. 7 is a transverse section taken through the base portion of the unit;

FIG. 8 is a top plan view of the unit;

DESCRIPTION OF INVENTION

Steamable Trays

Since the first embodiment of a freezer unit is loadable with pre-cooked food packages in the form of steamable trays, we shall first discuss the form of these trays.

Referring now to FIG. 1, there is shown a typical full-size steamable tray 10 made of aluminum foil. The tray has a rectangular configuration and is provided with a framelike flange 11 to which a removable metal foil cover is attached (not shown).

Tray 10 is filled with pre-cooked meals 12 which in FIG. 1 takes the form of twenty meal-filled pasta shells. The depth of the tray is such as to accommodate these shells. While all steamable full-size trays have the same rectangular dimensions, they vary in depth, depending on the height of the meals for which the trays are intended. Thus some standard trays are relatively shallow, others are of medium depth, and still others relatively deep. In practice, the freezer unit in accordance with the invention may be operated in conjunction with stainless steel trays and covers rather than metal foil trays, or with glass or ceramic trays, as long as the trays include a flange.

FIG. 2 illustrates the rectangular dimensions of a full-size tray 10 whose dimensions are, say, 20 by 12 inches with depths of $1\frac{1}{2}$, $2\frac{1}{2}$ and 4 inches. In practice, use can be made of half-size trays $10_a$ and $10_b$ as shown in FIG. 3; for together these 10 by 12 inch trays have the dimensions of a full-size tray and can be accommodated in the heat-up unit. Or use may be made of a set of three one-third size trays $10_c$, $10_d$ and $10_e$, as shown in FIG. 4; for these in combination have the dimensions of a full-size tray.

Freezer Unit for Steamable Trays

Figure 9:
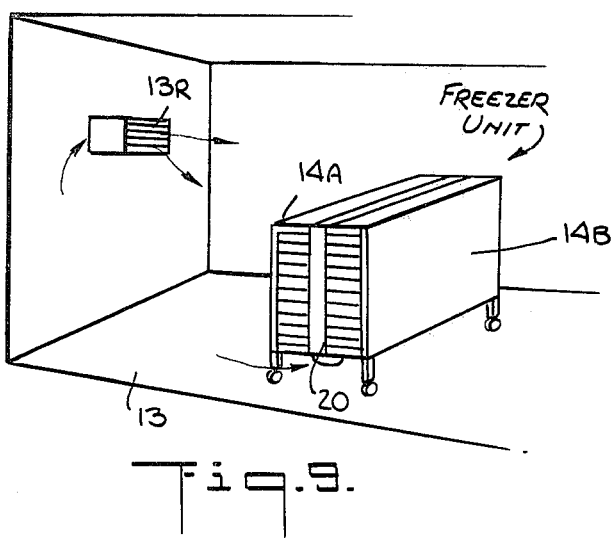
FIG. 9 shows a typical freezing closet or cold chamber having therein a freezer unit of the type shown in the above figures.

Referring now to FIGS. 5 to 8, there is shown a freezer unit for housing sealed steamable trays 10 having pre-cooked food therein. When the unit is wheeled into a cold chamber 13, as shown in FIG. 9, provided with a commercial refrigerator 13R, the unit then functions to draw cold air from the chamber atmosphere to rapidly freeze the pre-cooked food in the trays.

The unit includes an open frame having a pair of parallel vertical side walls 14A and 14B which are bridged by cross pieces 14C and 14D, and a rectangular base 15. The unit is provided with casters 17 so that it can conveniently be wheeled into and out of the freezing chamber. The frame is preferably fabricated of stainless steel or other easily cleaned material suitable for food handling.

Formed in the central region of the frame by a pair of spaced vertical panels 18 and 19 which lie parallel to side walls 14A and 14B is a plenum 20 having a rectangular cross section, panels 18 and 19 being perforated to admit air therethrough. Plenum 20 is provided at its lower end which is adjacent base 15 with a bank of three input ports 20A, each port having a shroud-like inlet 21 projecting therebelow. Disposed within each inlet 21 is a propeller 22 driven at high speed by a motor 23 mounted on base 15.

The rectangular output slot 20B of plenum 20 which lies at the upper end of the frame is selectively closeable by a vane 24. Vane 24 is operated by an electromagnetic actuator 25 which normally holds the vane in a horizontal position to shut the plenum. When energized, the actuator functions to position the vane vertically to open the plenum output to the atmosphere. A mechanically-driven cam or other means may be used for the same purpose.

Propellers 22 act to draw cold air from the atmosphere of the cold chamber and to force the air upwardly through the plenum. When vane 24 is positioned to open the plenum, the air propelled therethrough is discharged into the atmosphere. But when vane 24 is positioned to close the plenum, the air is confined to build up a positive pressure therein, the air being then forced laterally through the holes in plenum walls 18 and 19.

The region in the case between plenum panel 18 and side wall 14A constitutes a first freezer rack, and that between plenum panel 19 and side wall 14B a second freezer rack, the racks each being adapted to receive a stack of steamable trays. In order to stack steamable trays within each rack, brackets 26 are provided which are attached to side walls 14A and 14B. Seated on these brackets are wire grids 27 serving as open shelves, steamable trays 10 resting thereon. The brackets may be spaced to accommodate any standard tray depth. Since the frame is open, it is an easy matter to slide trays onto the shelves and to remove the trays from the shelves. The shelf arrangement in the racks is such as to create horizontal air spaces between the trays resting thereon.

Operation

In operation, when the loaded unit is wheeled into a cold chamber, atmospheric air at a temperature below the freezing point of the food is drawn into a unit by the driven propellers and forced upwardly through plenum 20 at high velocity. Because of plenum is alternately opened and closed by vane 24, the air, which is under positive pressure when the plenum is shut, is forced through the perforated plenum wall to flow at high velocity through the spaces between the trays before being returned to the chamber. The air returns directly to the chamber when the plenum is open.

In practice, the pulsatory rate may be a cycle per minute, each cycle having a thirty-second pulse period followed by a thirty-second no-flow interval or relaxation period. Optimum pulse wave rates and the relative duration of the flow and no flow periods in each cycle may be determined empirically to provide the desired heat transfer pattern for a given load of food.

In order to equalize the velocity of air through the holes in the plenum panels 18 and 19, the total pressure value must be over 0.1 inches of water column to generate an air stream having a velocity of no less than 1200 feet per minute. Thus during each pulse period when the plenum vane is shut, air flows at high velocity through the air spaces between the trays in the racks in opposite directions toward side walls 14A and 14B. This flow of cold air through the racks serves to promote rapid cooling of the food therein.

The pulsatory action expedites cooling in a manner which causes a reduction in the temperature of the body of the food which becomes substantially uniform throughout the body when the temperature level is close to the freezing point, thereby causing the body to freeze almost in toto within a relatively short period. In a conventional freezing process, freezing takes place in successive layers from the outside toward the core, as a consequence of which freezing is relatively slow and results in the formation of destructive ice crystals.

A typical body of pre-cooked food at ambient temperature or greater enclosed in a sealed container not only has a high moisture content, but also a substantial amount of air entrapped therein. To simplify the explanation of a pulsatory freezing process in accordance with the invention, we shall first treat this body of food as analogous to a body of water having air entrained therein.

If now a sealed container filled with this body of water is subjected to a continuous stream of cold air at, say, 0° F., flowing past the container at high velocity, because of heat then conducted from the warm body to the cold air stream, the temperature of the water body will go down. And because the heat differential is greatest between the outer zone or layer of the water body and the air stream, this layer will quickly freeze, whereas the warmer intermediate layers of the water body and its core will remain liquid.

Actually, of course, the water body is not layered, but for purposes of analysis with regard to the extraction of heat therefrom, if the entire body of water is initially at, say, 70° F., in order to transfer heat from the core of the body to the air stream, heat must be conveyed from the core to the surface of the body through what might be regarded as successive zones or layers, the layer closest to the surface being the outer layer.

Because in a conventional continuous flow freezing process, the outer layer of the body freezes first, this gives rise to stagnant films on the inner and outer surface of this solid layer, these films being created by entrapped air. Such films, as previously explained, resist heat transfer; and because the films are on either side of the frozen outer layer, the rate of heat transfer from the core and the intermediate layers to the air stream by way of the outer layer is then retarded. As a consequence, it then takes much longer to effect freezing of the core and intermediate layers. This protracted freezing time will result in the formation of large ice crystals which in the case of a food body will inflict serious damage on the internal food structure.

In the present invention, the containerized food body is not subjected to a continuous stream of cold air but to cold fluidic pulses which flow at high velocity and are separated by no-flow intervals. The outer layer of the food body which is in direct heat transfer relationship with the pulsed air stream is quickly reduced in temperature but not to the extent causing freezing, for the parameters of the pulsing action are such that in the no-flow intervals, heat is transferred from the relatively warm intermediate layers of the food body to the outer layer to prevent freezing thereof, this heat transfer resulting at the same time in a reduction in the temperature of the intermediate layers and a reduction of temperature in the core which concurrently transfer heat to the intermediate layers.

While this pulsatory action serves to bring about a transfer of heat from the core to the intermediate layers, and from the intermediate layers to the outer layer, and from the outer layer to the air stream, no internal film barriers are set up to resist this transfer, for the outer layer does not first freeze. And even if this pulsatory action gives rise to the incipient formation of an ice crust on the outer layer, this crust will fuse during the relaxation intervals of heat transfer from the intermediate layers.

As a consequence of such pulsed fluidic cooling, the core, the intermediate layers and the outer layers of the food body proceed to attain a temperature level approaching the freezing point which is nearly uniform throughout the body. When freezing thereafter takes place, this action occurs at about the same time. Thus the qualitative change from the liquid to the solid state takes place almost in toto within a short period, rather than in successive stages, thereby avoiding the formation of large ice crystals and the attendant destructive effects on the food.

In practice, a freezer unit in accordance with the invention may be programmed so that in an initial cooling phase, the high velocity air stream is continuously generated to accelerate a reduction in food temperature; but when the outer layer of the food body is then, say, within 10 degrees above the freezing point, the system is switched automatically from a continuous to a pulsatory air flow phase to carry out the nondestructive freezing technique in the manner previously described. The point at which this switchover takes place depends on the nature of the food body; for the salt, mineral and oil content of a food product determine its freezing point, this point varying from product to product.

Instead of a rotating vane to effect pulsing of the cold air, the air flow motor may be periodically energized, in which case the plenum is kept shut to cause air pressure to build up therein only in the periods in which the motor is operative.

In the unit shown in FIG. 1, the unit includes a blower motor; and if there are five units to go into a cold chamber, there will be five motors. In some installations, it may be desirable to provide units without motors, but with a ground inlet to the plenum input which when the unit is wheeled into a cold chamber is aligned with a respective register in a floor duct that leads to a common blower. Thus several motorless units may be placed in the chamber and supplied with air by the common motorized blower, each unit receiving air from a respective register. This reduces the cost and size of the individual units.

When a plurality of such units are operated from a common motorized blower, the registers which couple the blower duct to the units may be in louvered form and controlled to open and shut in sequence, thereby pulsing the cold air fed into the units. Thus assuming three units disposed over three registers leading to a common blower, in operation the first register is first opened to admit cold air only into the plenum of the first unit, the others being closed; then the second register is opened while the first and third are then shut to admit air only into the plenum of the second unit; and finally the third register is opened while the first and second are shut to admit air only into the plenum of the third unit, the cycle then being repeated. In this way, the three units are activated by a three-phase air flow system, the air in each unit being pulsed.

In practice, the same pulsatory technique may be used for freezing with brine or other liquid refrigerant rather than cold air to freeze fish, blood or other products. Thus assuming a unit with two wire baskets to hold fish, the brine may be circulated so as to flow at high velocity alternately past one basket and then the other, thereby rapidly pulse freezing the fish therein. In the case of whole blood, pulsatory freezing will prevent the formation of destructive ice crystals therein which otherwise render the blood useless for medical applications.

The above-described actions appear to be contradictory; for one would expect that a continuous flow of cold fluid at high velocity would give rise to more rapid heat transfer than the same fluidic stream interrupted periodically by no-flow intervals. However, the loss of cooling power during the no-flow intervals is more than compensated for by the absence of film barriers which would be produced when freezing occurs in successive layers and which act to slow down heat transfer.

While in the embodiment of the unit shown in FIGS. 5 to 8, the arrangement is such as to propel air upwardly in the plenum, in practice the unit may use a suction fan to periodically draw air into the plenum while it is shut to build up pressure therein, the air being discharged into the atmosphere in the intervals between pulses. Though the unit is designed for trays containing pre-cooked food, the same unit is usable for so-called retort pouches in which food such as chicken chow mein and beef stroganoff is cooked in flexible plastic pouches. After cooking, these retort pouches may be put on the shelves of the unit and wheeled into a cold room where they are quickly frozen.

Cartridges

Figure 11:
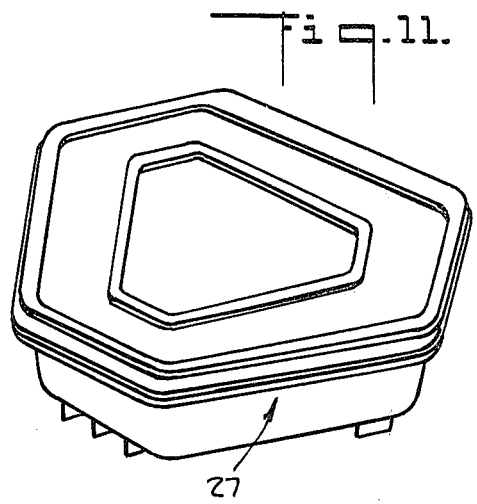
FIG. 11 is a perspective view of one of the hexagonal trays.
Figure 10:
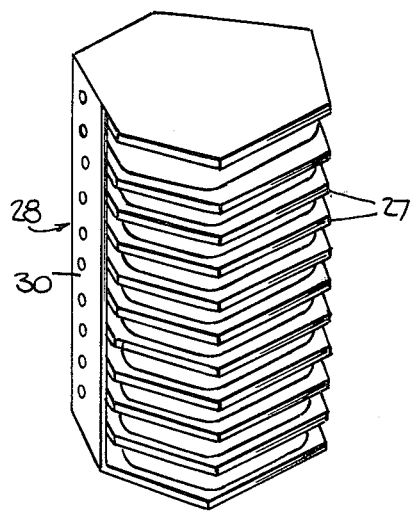
FIG. 10 illustrates, in perspective, a cartridge having a stack of hexagonal trays therein, which cartridge is to be loaded into a freezer unit adapted to receive a group of such cartridges.

Referring now to FIGS. 10 and 11, there is shown a food-loaded cartridge of the type disclosed in greater detail in the related patent applications. The cartridge is composed of an open carton 28 having nested therein a stack of sealed trays 29 containing pre-cooked meals.

Trays 29, which have a hexagonal formation, are provided with spacers to create air spaces between the trays in the stack. Carton 28 has three rear sides, only side 30 being visible in FIG. 10, the three rear sides being angled to conform to the corresponding rear sides of the rays. Thus the upper and lower ends of the carton have a hexagonal form corresponding to that of the trays, the open carton exposing the three front sides of the trays in the stack.

The rear sides of the carton each have a vertical row of ventilation holes therein to permit cold air blown therethrough to pass into the spaces between the stacked trays. Thus the cartridge constitutes a convenient package of food-loaded trays to facilitate handling and storage.

Freezer Unit for Cartridges

Figure 12:
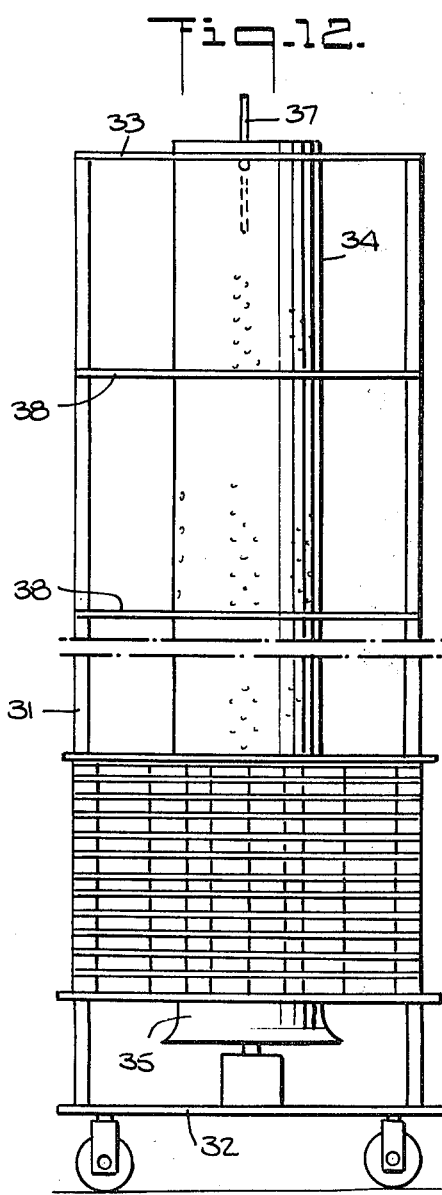
FIG. 12 is an elevational view, partly in section, of a freezer unit for cartridges.
Figure 13:
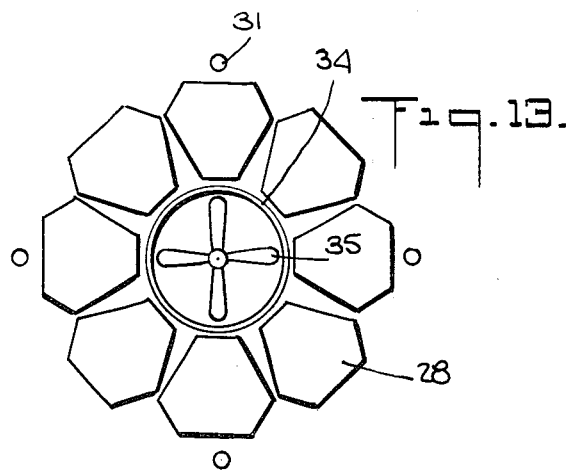
FIG. 13 is a transverse section taken through the FIG. 11 unit.

The freezer unit shown in FIGS. 12 and 13 is adapted to process cartridges of the type shown in FIG. 10. The unit in this instance is provide with a tall cylindrical open frame formed by a circular array of rods 31 anchored on a base 32 mounted on casters 33 so that the unit can be wheeled into a cold chamber.

The plenum for this unit takes the form of a tube 34 coaxially disposed within the open cylindrical frame, the tube being perforated. The input of the tubular plenum is provided with a shroud-like inlet 35 within which is disposed a propeller 35 driven by a motor 36 mounted on base 32. A vane 37 is supported within the output of the plenum, the vane being operated by a solenoid or other means (not shown) to alternately open and shut the plenum to produce a pulsatory wave of cold air to freeze the food in the trays.

The rack for receiving the cartridges is defined by the annular region between the tubular plenum and the rods 31 of the open frame. This rack is provided with shelves 38 at different levels, the spacing between shelves being appropriate to the height of the cartridges. The cartridges on the shelves are arranged in an annular array, with the rear walls of the cartons encircling the perforated tubular plenum, as shown in FIG. 13.

The operation of the cartridge freezer unit is essentially the same as the steamable unit. Propeller 35 draws cold air from the atmosphere of the cold chamber and forces the air upwardly in the plenum, the air being discharged into the chamber when vane 37 is open. When vane 37 is positioned to shut the plenum, the cold air is then forced laterally through the holes in the plenum tube. Because of the positive pressure created in the shut plenum, the air is projected at high velocity through the air spaces between the trays in the cartridges, the air then returning to the chamber.

While there has been shown and described a preferred embodiment of a freezing unit for pre-cooked food packages in accordance with the invention, it will be appreciated that many changes and modifications may be made therein without, however, departing from the essential spirit thereof. Thus while the units have been described as freezer units, they are also capable of functioning in the environment of hot chambers as heat-up units for cold food. In that case, the heating units will act to draw heated atmospheric air from the chamber and to circulate this air in a pulsatory flow pattern through the food-loaded racks. Since the freezing of warm food and the heating of cold foot both involve heat transfer between a solid body and a fluid, the same factors which control the rate of heat transfer come into play, whether the unit functions as a heat-up or cool-down device.

As is well known, the amount of energy required to raise or lower the temperature of a liquid from one level to another is much smaller than the amount involved during a change in state which takes place at a constant temperature. Thus at its melting point, ice absorbs about 144 BTU's as it passes into its liquid state and when the liquid is again frozen, the same amount of BTU's is liberated. The energy absorbed or liberated by a unit mass of liquid during a change of state is referred to as its latent heat. In a freezer unit in accordance with the invention, when the food being frozen approaches the freezing point, as sensed by a suitable detector, the detector may be used to signal a motor control circuit which then acts to switch off the vane or other means producing a pulsatory action and at the same time act to increase the air blower speed and the resultant volume of cold air drawn into the unit whereby the blower then functions in a continuous mode as the liquid constituents of the food are about to undergo a change of state, thereby providing the necessary latent heat therefor.

I claim:

1. A freezer unit usable in a cold chamber having an atmosphere of cold air whose temperature is below the freezing point, the unit being adapted to freeze food packages and comprising:

A an open frame;
   B A vertical plenum mounted within said frame, said plenum being provided with a perforated wall and having an input and a closeable output;
   C a rack within said frame adjacent said perforated wall to receive a stack of food packages with horizontal spaces therebetween; and
   D means to draw cold air from the atmosphere of the chamber and to force the air into the input of the plenum to create a positive pressure therein when the plenum is closed whereby the air is projected at high velocity through the holes in the plenum wall into the spaces between the food packages to effect rapid cooling thereof.

2. A unit as set forth in claim 1, wherein said food packages are constituted by steamable trays containing precooked food.

3. A unit as set forth in claim 1, wherein said food packages are constituted by cartridges, each constituted by a ventilated carton having a stack of food-loaded trays contained therein, the trays in said stack being spaced from each other.

4. A unit as set forth in claim 1, further including means to alternately close and open the output of said plenum to cause the air projected through the holes to assume a pulsatory form constituted by periodic high velocity pulses of cold air separated by no-flow intervals to produce a heat transfer pattern causing the body of food to freeze almost in toto within a relatively short period.

5. A unit as set forth in claim 1, wherein said frame has a pair of parallel vertical sides, and said plenum is formed by a pair of perforated walls parallel to the vertical sides, a rack being formed between each plenum wall and the related side of the frame.

6. A unit as set forth in claim 5, wherein each rack is defined by brackets secured to the walls and sides to support open shelves for accommodating said packages.

7. A unit as set forth in claim 5, wherein said open input is formed by at least one port having a shroud-like inlet within which is a motor-driven propeller that serves to draw atmospheric air from the chamber and direct it into the plenum.

8. A unit as set forth in claim 5, wherein said output is provided with a vane which in its horizontal position closes said plenum and in its vertical position opens said plenum.

9. A unit as set forth in claim 8, further including electromagnetic means to actuate said vane at a predetermined periodic rate.

10. A unit as set forth in claim 5, further including casters at the base of the frame to render the unit wheelable.

11. A unit as set forth in claim 1, wherein said frame is cylindrical and said plenum is formed by a perforated tube coaxially disposed within said frame, the rack being formed in the annular region between the tube and the frame.

12. A unit as set forth in claim 11, further including a vane disposed in the output of said plenum to alternately open and close the plenum.

13. A unit as set forth in claim 11, wherein the input of said plenum has a shroud-like inlet having a propeller disposed therein to draw said atmospheric air from the chamber and force it into the plenum.

14. A unit as set forth in claim 1, wherein said rack is provided with shelves to receive an annular array of cartridges surrounding said tube, each cartridge being constituted by a ventilated carton within which is nested a stack of food-loaded trays with spaces therebetween.

15. The method of rapidly freezing a freezable organic product which initially is at a temperature well above the freezing point in a manner minimizing the formation of large ice crystals therein, the method comprising the steps of:

A subjecting the product to a stream of fluid flowing at high velocity whose temperature is below the freezing point of the product;
   B periodically interrupting the flow to produce fluidic pulses separated by no-flow intervals to create a heat transfer pattern within the body of the product resulting in a reduction in temperature which becomes substantially uniform throughout the body at a level close to the freezing point whereby when freezing thereafter takes place in the body, it freezes almost in toto within a relatively short period to avoid the formation of large ice crystals.

16. The method as set forth in claim 15, in which said product is a package of pre-cooked food.

17. The method as set forth in claim 15, wherein said fluid is cold air which is forced into a closeable, perforated plenum to create a positive pressure therein causing the air to be projected at high velocity through the perforations, the plenum being periodically opened to produce said interruptions.

18. The method as set forth in claim 15 for freezing a plurality of products, the fluid flow being sequentially and cyclically directed from one product to another in the plurality thereof, whereby when one product is subjected to flow, flow to the other products is interrupted.

19. The method as set forth in claim 1, wherein said fluid is brine.

20. The method as set forth in claim 15, further including the steps of switching off the periodic interruption of the flow and at the same time increasing the volume of the fluid stream, this step taking place when the product reaches the level close to the freezing point to furnish the latent heat required for the change of state.

* * * * *